United States Patent
Carrillo Fuentevilla et al.

(10) Patent No.: US 9,011,144 B2
(45) Date of Patent: Apr. 21, 2015

(54) PALATAL T-BAR

(76) Inventors: Roberto Carrillo Fuentevilla, Nuevo Leon (MX); Roberto Jose Carrillo Gonzalez, Nuevo Leon (MX)

(*) Notice: Subject to any disclaimer, the term of this patent is extended or adjusted under 35 U.S.C. 154(b) by 0 days.

(21) Appl. No.: 13/232,461

(22) Filed: Sep. 14, 2011

(65) Prior Publication Data

US 2013/0065191 A1   Mar. 14, 2013

(51) Int. Cl.
  A61C 7/00     (2006.01)
  A61C 8/00     (2006.01)
(52) U.S. Cl.
  CPC .................. *A61C 7/00* (2013.01); *A61C 8/0096* (2013.01)
(58) Field of Classification Search
  CPC ............ A61C 5/007; A61C 7/00; A61C 7/08; A61C 7/10; A61C 7/12; A61C 7/14; A61C 7/145; A61C 7/146; A61C 7/16; A61C 8/00; A61C 8/0018; A61C 8/0022; A61C 8/005; A61C 8/0075; A61C 8/0096
  USPC ..................... 433/2, 7, 9, 18, 21, 24, 173, 174
  See application file for complete search history.

(56) References Cited

U.S. PATENT DOCUMENTS

| | | | |
|---|---|---|---|
| 4,392,826 A | | 7/1983 | Goshgarian |
| 4,408,989 A | | 10/1983 | Cleary |
| 4,413,978 A | * | 11/1983 | Kurz .................................. 433/6 |
| 4,522,590 A | * | 6/1985 | Pletcher .......................... 433/15 |
| 4,592,725 A | | 6/1986 | Goshgarian |
| 4,854,864 A | | 8/1989 | Cleary |
| 5,002,485 A | | 3/1991 | Aagesen |
| 5,066,224 A | | 11/1991 | Block et al. |
| RE35,170 E | | 3/1996 | Arndt et al. |
| 5,697,781 A | | 12/1997 | Ellingson |
| 5,785,520 A | | 7/1998 | Carano et al. |
| 5,829,970 A | | 11/1998 | Yousefian |
| 5,938,437 A | | 8/1999 | DeVincenzo |
| 5,967,772 A | | 10/1999 | Gray |
| 6,033,217 A | | 3/2000 | Shirasuka |
| 6,193,509 B1 | | 2/2001 | DeVincenzo |
| 6,435,870 B1 | | 8/2002 | Walde |
| 6,568,935 B2 | * | 5/2003 | Clark ............................... 433/18 |
| 6,626,665 B1 | | 9/2003 | Keles |
| 6,719,557 B1 | | 4/2004 | Williams |
| 6,896,516 B2 | | 5/2005 | Lin et al. |
| 6,908,306 B2 | | 6/2005 | Bowman et al. |

(Continued)

FOREIGN PATENT DOCUMENTS

WO    WO 2010059407 A1 *  5/2010  ............... A61C 7/22

*Primary Examiner* — Cris L Rodriguez
*Assistant Examiner* — Justin O'Donnell
(74) *Attorney, Agent, or Firm* — Caesar, Rivise, Bernstein, Cohen & Pokotilow, Ltd.

(57) ABSTRACT

A palatal t-bar for preventing movement of selected teeth during corrective movement of other teeth through the use of an orthodontic appliance such as orthodontic braces. The t-bar comprises an elongate stem having an anchorage end arranged for affixation to the palatal bone of a patient by means of a temporary bone anchorage device, e.g., a miniscrew implant, and a free end extending in an anterior direction from the anchorage end. The stem is shaped to conform to the palatal surface of the patient. A cross-bar extends laterally from the free end of the stem and is arranged to engage one or more selected maxillary anterior teeth to retain the teeth nonmobile and non-rotational during corrective movement of other teeth utilizing an orthodontic appliance such as orthodontic braces.

14 Claims, 3 Drawing Sheets

(56) References Cited

U.S. PATENT DOCUMENTS

| | | |
|---|---|---|
| 7,094,051 B2 | 8/2006 | Williams |
| 7,771,196 B2 | 8/2010 | Weissbach Otte |
| 2003/0044746 A1* | 3/2003 | Marotta et al. ............ 433/18 |
| 2004/0152035 A1* | 8/2004 | Bumann et al. ............ 433/18 |
| 2008/0050691 A1* | 2/2008 | Baughman et al. ............ 433/18 |
| 2010/0015565 A1* | 1/2010 | Carrillo Gonzalez et al. .... 433/7 |
| 2010/0143855 A1 | 6/2010 | Scheffler |

* cited by examiner

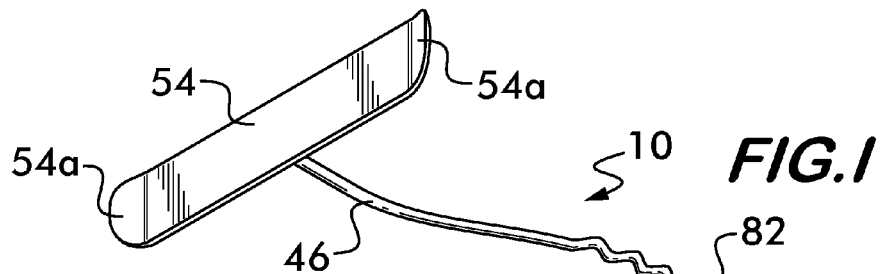
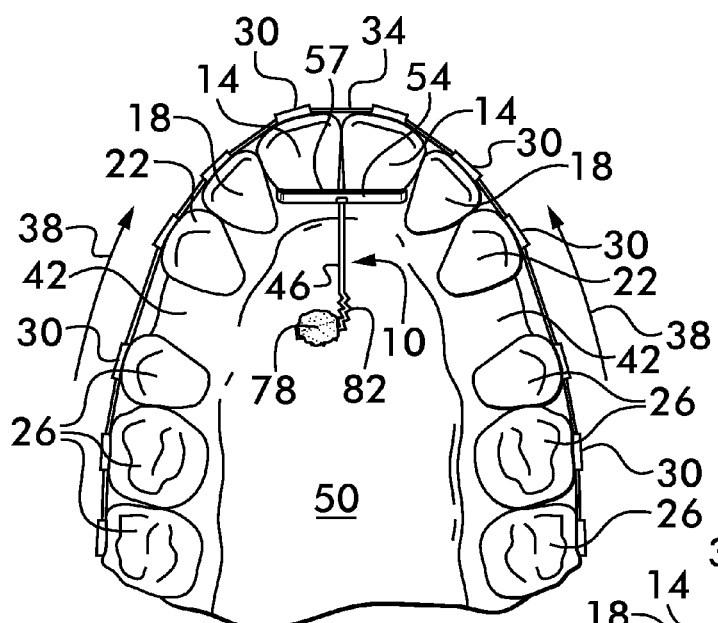
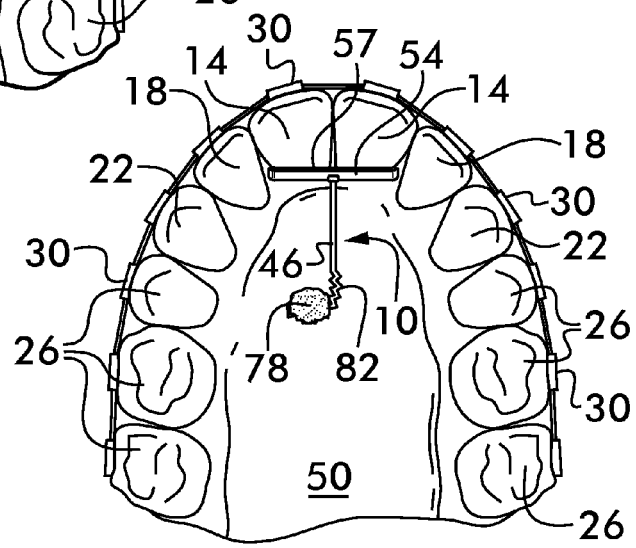

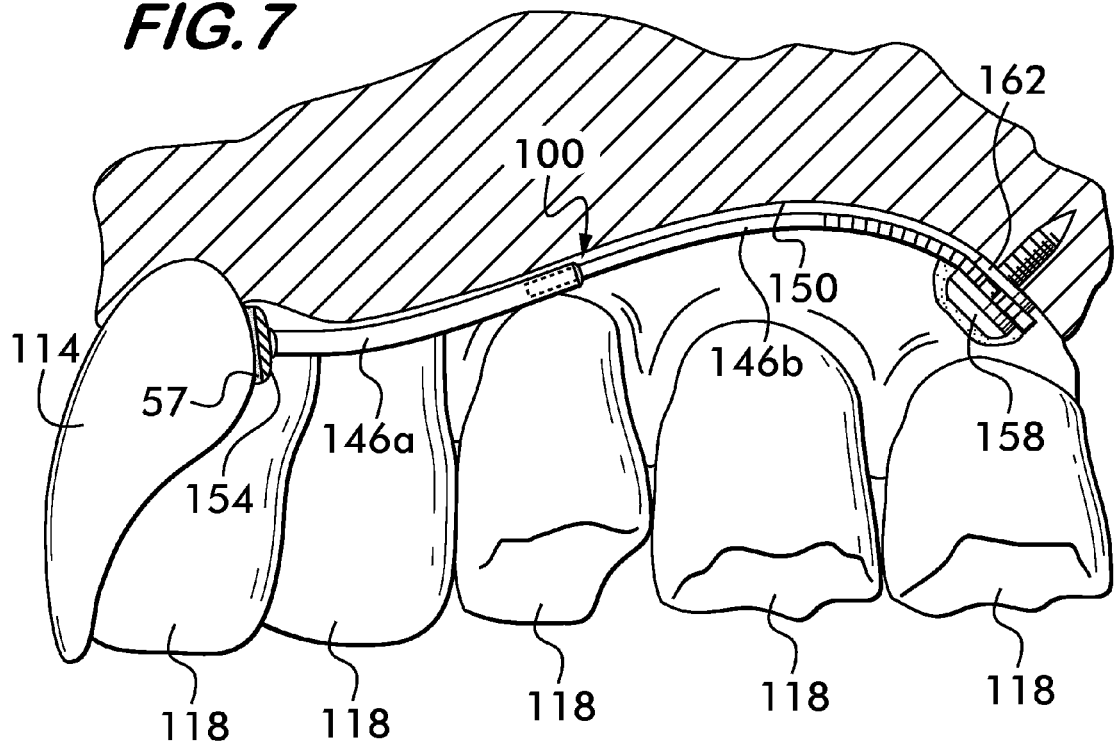
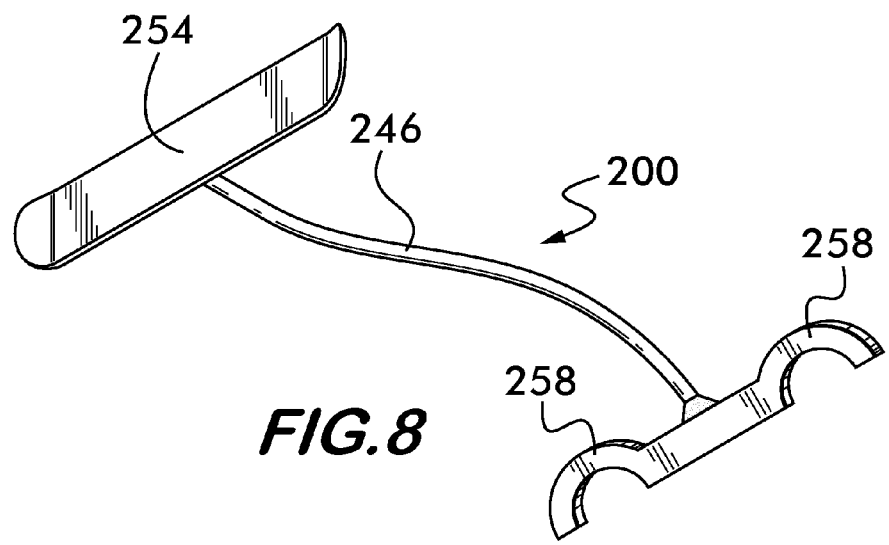

PALATAL T-BAR

CROSS-REFERENCE TO RELATED APPLICATIONS

"Not Applicable"

STATEMENT REGARDING FEDERALLY SPONSORED RESEARCH OR DEVELOPMENT

"Not Applicable"

INCORPORATION-BY-REFERENCE OF MATERIAL SUBMITTED ON A COMPACT DISK

"Not Applicable"

FIELD OF THE INVENTION

Background of the Invention

To clarify the description of the invention, certain dental terms should be understood. Upper and lower teeth are termed maxillary and mandibular teeth, respectively. Front teeth are anterior teeth and back teeth are posterior teeth. Anterior teeth are incisors and are named centrals, laterals, and cuspids in order from the anterior midline to the posterior. The posterior teeth, from anterior to posterior, are first and second premolars and first, second, and third molars. Distal refers to the direction towards the last posterior tooth, as opposed to mesial, which refers to the direction towards the anterior midline.

Orthodontists and dental researchers are constantly searching for new and improved ways to correct malocclusion problems. Corrective movement of teeth may be accomplished utilizing a variety of orthodontic appliances. One such commonly used orthodontic appliance is orthodontic braces, wherein brackets are bonded to teeth and an arch wire is attached to the brackets in known ways. The arch wire exerts pressure on the brackets and teeth whereby the positioning of teeth relative to each other can be controlled and adjusted. The adjustment of the position of teeth is accomplished by providing forces in a desired direction. For many desired forces, there are unwanted reciprocal forces that often move teeth from their correct position.

Attempts have been made to try to secure teeth from moving, rotating, or torquing from their correct positions in response to such unwanted forces. However, often these attempts are expensive, or involve surgery typically requiring significant healing time. Thus, there exists a need for an orthodontic system to position and adjust a tooth or teeth of a patient that is able to withstand occlusal, biomechanic or other reciprocal forces applied thereto, is less expensive and time consuming to install, and is less invasive to the patient. It is to the provision of such an improved orthodontic anchor system that the present invention is primarily directed.

SUMMARY OF THE INVENTION

A palatal t-bar for preventing movement of selected teeth during corrective movement of other teeth through the use of an orthodontic appliance such as orthodontic braces is provided. The t-bar comprises an elongate stem having an anchorage end arranged for affixation to the palatal bone of a patient by means of a temporary bone anchorage device, e.g., a miniscrew implant, and a free end extending in an anterior direction from the anchorage end. The stem is shaped to conform to the palatal surface of the patient. A cross-bar extends laterally from the free end of the stem and is arranged to engage one or more selected maxillary anterior teeth to retain the teeth non-mobile and non-rotational during corrective movement of other teeth utilizing an orthodontic appliance such as orthodontic braces.

DESCRIPTION OF THE DRAWINGS

FIG. 1 is an isometric view of a preferred embodiment of the palatal t-bar of the present invention;

FIG. 2 is a view of the preferred embodiment of the palatal t-bar of the present invention installed in the roof of the mouth of a patient, the patient also wearing orthodontic braces;

FIG. 3 is a view of the preferred embodiment of the palatal t-bar of the present invention installed within the roof of the mouth of a patient, the patient also wearing orthodontic braces;

FIG. 7 is an elevational view, partially in cross-section, illustrating a second embodiment of the palatal t-bar of the present invention installed within the roof of the mouth of a patient; and, FIG. 8 is an isometric view of a third embodiment of the palatal t-bar of the present invention.

DETAILED DESCRIPTION OF THE PREFERRED EMBODIMENT

Figure 4:
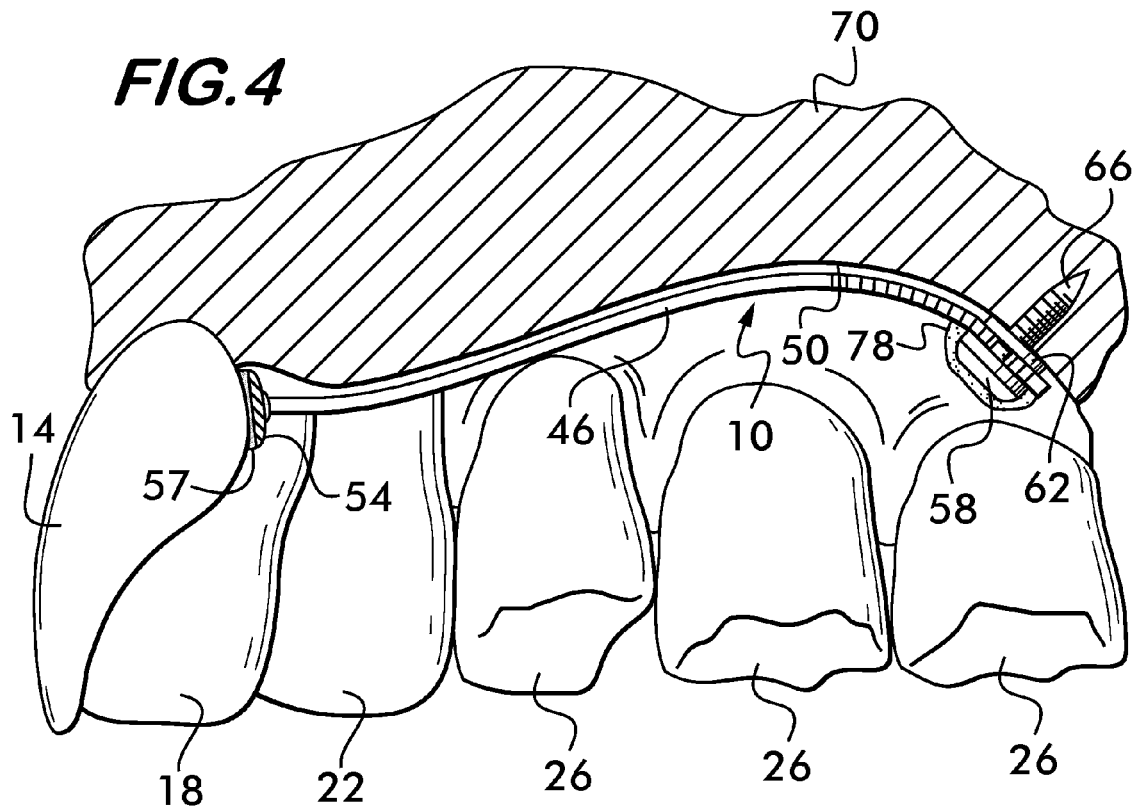
FIG. 4 is an elevational view, partially in cross-section, illustrating the preferred embodiment of the palatal t-bar of the present invention installed within the roof of the mouth of a patient.

Referring now in greater detail to the drawings in which like numerals represent like components throughout the several views, FIGS. 1-4 illustrate a first preferred embodiment of the palatal t-bar 10 of the present invention. As best shown in these figures, the palatal t-bar 10 is intended for placement within the mouth of a patient to serve as an anchorage to prevent one or more selected teeth (as an example here shown on teeth 14) anchored within the t-bar 10 from rotating, torquing, or moving distally during corrective movement of other teeth. Such other teeth may include lateral incisors 18, canines 22, or posterior teeth 26. As shown in FIGS. 1-4, corrective movement of teeth 14, 18, 22, and 26 is shown as being accomplished utilizing orthodontic braces, wherein brackets 30 are bonded to teeth 14, 18, 22, and 26 and an arch wire 34 is attached to the brackets 30 in known ways. The arch wire 34 exerts pressure on the brackets 30 and teeth 14, 18, 22, 26 whereby the positioning of teeth relative to each other can be controlled and adjusted. The adjustment of the position of the teeth is accomplished by providing forces in a desired direction.

Referring now to FIG. 2, the orthodontic braces are shown mounted to the patient's maxillary teeth at the start of a corrective orthodontic procedure to provide corrective forces to move the posterior teeth 26, e.g., premolars and molars, anteriorly in the direction of arrows 38 to fill in gaps 42 existing between the teeth 22 and 26. During movement of the posterior teeth 26 in the mesial direction of arrows 38, undesired forces may inadvertently be applied to the teeth 14 providing a tendency for them to rotate, torque, or move in an undesired direction.

To prevent such unwanted rotation, torque or movement of these teeth 14, the palatal t-bar 10 is provided. Referring again to FIGS. 1-4, the palatal t-bar 10 includes a cylindrical elongate stem 46 having a first end arranged to be affixed to the palatal surface 50 of the patient and a second end to which a cross-bar 54 is attached. Alternatively, the cross-bar 54 may be integral with the elongate stem 46. As best shown in FIGS. 1 and 4, the elongate stem 46 is comfortable for the patient and generally cylindrical in shape. The elongate stem 46 can be contoured, molded or shaped to roughly match the palatal surface 50. The cross-bar 54 is shaped to match the contour of the posterior surface of one or more anterior teeth 14, 18 and/or 22 in their correct position. In this manner, the cross-bar 54 will prevent movement, rotation and torquing of the anchored teeth. In addition, the cross-bar 54 includes curved ends 54a (FIG. 1) arranged for bending around the edges of the anchored teeth 14 to prevent movement of the anchored teeth 14. As best shown in FIGS. 2 and 3, the cross-bar 54 is bonded or held to one or more anchored teeth 14, 18 and/or 22 utilizing a suitable dental adhesive 57 to provide support for teeth 14 against the aforementioned undesired forces.

Although the cross-bar 54 is illustrated in FIGS. 1-4 as anchoring only the two frontmost teeth 14, i.e., the upper central incisors, it should be understood that the cross-bar 54 could be configured to anchor a smaller or larger number of teeth during the application of corrective orthodontic forces to other teeth. For example, the cross-bar 54 could be lengthened and suitably configured to anchor the upper lateral incisors 18 in addition to the upper central incisors 14 to prevent unwanted distal movement, rotation or torquing of these teeth during the application of corrective forces. Likewise, the cross-bar 54 could be lengthened and configured to anchor upper canines 22 in addition to the central and lateral incisors, 14 and 18.

The palatal t-bar 10 is formed from a metal such as titanium, titanium alloys, stainless steel, a nickel-titanium alloy, titanium-molybdenum alloy, a chromium-nickel alloy, or combinations thereof, or alternatively, could be formed from synthetic polymer materials, such as an acrylic or by stereolithography. In the embodiment shown in FIGS. 1-4, the palatal t-bar 10 is illustrated as including an elongate stem 46 that is contoured to the shape of the maxilla, but it will be understood that other shapes or configurations can be used.

Figure 6:
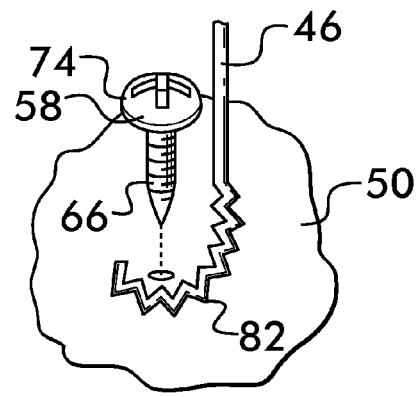
FIG. 6 is another view of the stem portion of the palatal t-bar of the present invention.

As best shown in FIG. 4, the palatal t-bar 10 includes an anchor mechanism for anchoring the t-bar 10 to the patient's palatal surface 50, i.e., the roof of the patient's mouth. As shown in FIGS. 4 and 6, under the present embodiment, the anchor mechanism includes an anchoring miniscrew implant 58 to which one end of the palatal t-bar is fixed. As an optional feature, in case it is necessary, a washer 62 can be used to provide a small amount of space or separation, e.g., 1 mm, between the palatal t-bar 10 and the palatal surface 50 when the t-bar 10 is anchored to the maxillary bone. In this manner, the palatal t-bar 10 will not contact the roof of the patient's mouth during use which will increase the patient's level of comfort, thus allowing for saliva to pass over the t-bar and facilitating hygiene around the miniscrew implant 58. The anchoring miniscrew implant 58 and washer 62 are minimal in size so as to be unobtrusive of eating and to likewise minimize the trauma to the tongue and palate of the patient during insertion and thereafter while the palatal t-bar 10 is worn by the patient. Accordingly, the anchoring miniscrew implant 58 typically will be approximately 8 to 21 mm in length with approximately 2 to 6 mm of the anchoring miniscrew implant 58 being exposed outside the palatal surface 50 when inserted in the patient's mouth. However, it is possible to use anchors of other, varying dimensions and types. Therefore, while the present anchor mechanism is being disclosed with reference to a preferred range of sizes, such a preferred range is for illustrative purposes only and it will be understood by those skilled in the art that various other types of conventional dental implants and varying sizes also may be used.

As shown, the anchoring miniscrew implant 58 typically includes a body 66 that is inserted or drilled into the palatal surface 50 of the mouth of the patient so as to be embedded into the palatal bone 70, and a head or upper portion 74 exposed from the palate. The shank portion 66 of the anchoring miniscrew implant 58 further typically include threads to enable the anchoring miniscrew implant 58 to be drilled into the palatal surface 50, although it will be understood by those skilled in the art that the anchoring miniscrew implant 58 also can have substantially smooth sided shanks. As best shown in FIGS. 2-4, a coating or bonding material 78 is utilized to mechanically hold the elongate stem 46 of the t-bar 10 to the miniscrew implant 58. Also, a mechanical retention can be obtained by using metallic ligature wire to hold the elongate stem 46 of the t-bar 10 to the miniscrew implant 58.

Figure 5:
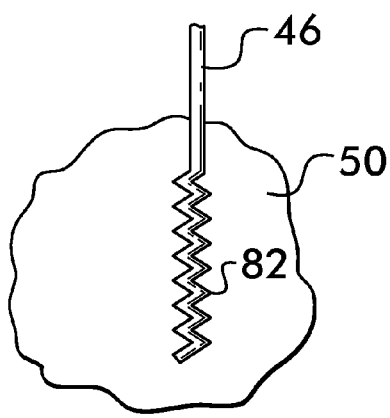
FIG. 5 is a view of the stem portion of the palatal t-bar of the present invention.

As best illustrated in FIGS. 3-6, a portion of the elongate stem 46 may be configured as a bendable spine 82 formed in a notched or zig-zag pattern to provide a plurality of retention surfaces to enable mechanical retention with the bonding material 78. The bendable spine 82 may be integral with or attached to the elongate stem 46 and may be fabricated of the same or different materials as the elongate stem 46. The bendable spine 82 is bendable in proximity to the anchoring miniscrew implant 58, which serves as a locator. As best shown in FIGS. 4-6, the spine 82 is bent around the head, neck or body 66 of the anchoring miniscrew implant 58. Thereafter, it is secured to the miniscrew implant 58 by using a ligature wire, bonding material or composite 78. The bonding material 78 flows within the retention grooves of the bendable spine 82 to create a solid mechanical retention between the t-bar 10 and the miniscrew implant 58. By providing a bendable spine 82, the palatal t-bar 10 is provided with a degree of adjustability to assure that anchorage can occur while the cross-bar 54 engages the teeth 14 to be anchored.

FIG. 3 illustrates the patient's maxillary teeth at the conclusion of the corrective orthodontic procedure wherein the posterior teeth 26 have been moved mesially to eliminate gaps between teeth 22 and 26. As illustrated in FIG. 3, the t-bar 10 anchoring the maxillary teeth 14 has prevented these teeth 14 from rotating, torquing, or moving distally during corrective mesial movement of the posterior teeth 26. The above example illustrates use of the t-bar 10 for anchoring teeth 14 during mesial movement of other teeth, e.g., molars. However, it should be understood that the t-bar 10 would be equally effective for anchoring teeth 14 during distal movement of other teeth, such as molars, utilizing dental appliances such as braces.

Referring now to FIG. 7, there is shown a second embodiment of the palatal t-bar of the present invention. As with the first embodiment, the second embodiment t-bar 100 is intended for placement within the mouth of a patient to prevent teeth 114 anchored within the second embodiment t-bar from rotating, torquing, or moving mesially or distally during corrective movement of other teeth 118. As with the first embodiment, the second embodiment palatal t-bar includes a cross-bar 154 that is attached to, or integral with an elongate stem. The cross-bar 154 is bonded or held to one or more anchored teeth, e.g., the anchored teeth 114 shown in FIG. 7, utilizing a suitable dental adhesive 57 to provide support for the teeth against the undesired forces discussed above.

However, under the embodiment 100, the elongate stem is formed of a multi-piece construction, e.g., a two-piece construction, including an outer portion 146a and an inner portion 146b that are in telescoping relation to each other to enable adjustability of the overall length of the elongate stem to accommodate different sized palates. Once the overall length has been determined, the inner and outer portions may be crimped, glued or soldered together to retain the elongate stem at a defined length. The elongate stem includes a contour that roughly matches the maxilla 150 and includes a fixed end that is arranged to be anchored to the maxilla 150 utilizing anchoring hardware, e.g., an anchoring screw 158. A washer 162 may be used to provide a small amount of separation between the second embodiment palatal t-bar and the maxilla 150 for the reasons previously discussed. Likewise, the anchoring screw 158 may be coated with a coating or bonding mechanism similar to that shown in the first embodiment for the reasons previously discussed.

Referring now to FIG. 8, there is shown a third embodiment 200 of the present invention. This third embodiment 200 of the palatal t-bar is similar to prior embodiments in that it is intended for placement within the mouth of a patient to serve as an anchorage for preventing teeth anchored therein from rotating, torquing, or moving distally during corrective movement of other teeth. As with the prior embodiments, the third embodiment palatal t-bar 200 includes a cross-bar 254 that is attached to, or integral with an elongate stem 246. However, under this embodiment 200, the elongate stem 246 includes an anchorage end that will fit two anchors, as opposed to one, and includes two semi-circular anchoring openings 258 that serve as points for anchoring the third embodiment palatal t-bar 200 within the maxilla utilizing suitable anchorage hardware as previously discussed. By providing two anchoring openings 258, as opposed to one, lateral support for the anchored teeth will be increased to further reduce the possibility of torquing, rotation, or distal movement of the anchored teeth during application of corrective orthodontic forces.

In the foregoing specification, specific embodiments of the present invention have been described. However, one of ordinary skill in the art appreciates that various modifications and changes can be made without departing from the scope of the present invention. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention. Accordingly, the specification and figures are to be regarded in an illustrative rather than a restrictive sense, and all such modifications are intended to be included within the scope of present invention.

We claim:

1. A palatal system to prevent movement of selected teeth of a human during corrective movement of other teeth through the use of an orthodontic appliance, said palatal system comprising:
   a. a bone anchorage device arranged for locating in the palatal midline surface of a patient;
   b. a single elongate stem having a generally cylindrical cross-section and having an anchorage end arranged for affixation to said bone anchorage device and a free end extending in an anterior direction from said anchorage end, said stem being formed in an S-shaped curve to conform to the palatal arch of the patient wherein said single elongate stem includes a retention structure to facilitate affixation of said stem to said bone anchorage device, wherein said retention structure is a spine arranged to wrap around said bone anchorage device, said spine comprising a zig-zag configuration providing retention surfaces; and,
   c. a cross-bar extending laterally in opposite directions from the free end of said stem, wherein said elongate stem and said cross-bar together form an uppercase T-shape, said cross-bar arranged to engage two or more selected adjacent teeth to retain said teeth non-mobile and non-rotational during corrective movement of other teeth utilizing an orthodontic appliance, said cross-bar comprising a generally flat and rectangle-shaped central portion that remains generally flat and unbent and is extendable across said two or more selected adjacent teeth, and opposed curved ends extending from said central portion, said curved ends arranged for bending around the edges of said two or more selected adjacent teeth to be anchored, said generally flat and rectangle-shaped central portion of said cross-bar intersecting the free end of said stem.

2. The palatal system of claim 1, wherein said elongate stem and cross-bar are of an integral construction and fabricated from a material selected from the group consisting of titanium, titanium alloy, stainless steel, chromium-nickel alloys, non-ferrous metals, materials resulting from stereolithographic processing and combinations thereof.

3. The palatal system of claim 1, wherein said cross-bar is arranged to engage upper central incisors.

4. The palatal system of claim 3, wherein said cross-bar is arranged to additionally engage upper lateral incisors.

5. The palatal system of claim 4, wherein said cross-bar is arranged to additionally engage upper canines.

6. The palatal system of claim 1, wherein said bone anchorage device comprises an anchorage miniscrew implant.

7. The palatal system of claim 6, additionally comprising a quantity of flowable filling material arranged to encapsulate said anchorage miniscrew implant and arranged to flow between said retention surfaces of said retention structure to create a solid bond between said anchorage miniscrew implant and said stem.

8. The palatal system of claim 7, wherein said anchorage end of said elongate stem is arranged for affixation at or off a center-line of the patient's maxilla.

9. The palatal system of claim 1, wherein said bone anchorage device comprises a bone anchor.

10. The palatal system of claim 1, additionally comprising a washer configured to be disposed between said elongate stem and the patient's maxilla to provide space between said elongate stem and the patient's maxilla, to prevent said palatal system from touching the patient's palate.

11. The palatal system of claim 10, wherein said washer is approximately 1 mm in thickness.

12. The palatal system of claim 11, wherein said washer is configured to be disposed between said elongate stem and the patient's palate.

13. The palatal system of claim 1, wherein said elongate stem comprises an inner portion in telescoping relation to an outer portion to enable adjustability of overall length of said stem to accommodate different sized palates.

14. The palatal system of claim 1, wherein said cross-bar is arranged for securement to said two or more selected teeth by a dental adhesive.

* * * * *